US012766330B2

(12) United States Patent
Müller-Bruhn

(10) Patent No.: US 12,766,330 B2
(45) Date of Patent: Oct. 20, 2026

(54) STIMULATION ARRANGEMENT AND METHOD OF ACTIVATING A PATIENT

(71) Applicant: STIMIT AG, Biel/Bienne (CH)

(72) Inventor: Ronja Müller-Bruhn, Windisch (CH)

(73) Assignee: STIMIT AG, Biel/Bienne (CH)

( * ) Notice: Subject to any disclaimer, the term of this patent is extended or adjusted under 35 U.S.C. 154(b) by 898 days.

(21) Appl. No.: 17/917,386

(22) PCT Filed: Apr. 9, 2021

(86) PCT No.: PCT/EP2021/059259
§ 371 (c)(1),
(2) Date: Oct. 6, 2022

(87) PCT Pub. No.: WO2021/204981
PCT Pub. Date: Oct. 14, 2021

(65) Prior Publication Data

US 2023/0173290 A1 Jun. 8, 2023

(30) Foreign Application Priority Data

Apr. 9, 2020 (CH) .................................... 00433/20

(51) Int. Cl.
*A61N 2/00* (2006.01)
*A61M 16/00* (2006.01)
*A61N 2/02* (2006.01)

(52) U.S. Cl.
CPC ......... *A61N 2/004* (2013.01); *A61M 16/0003* (2014.02); *A61N 2/002* (2013.01); *A61N 2/02* (2013.01)

(58) Field of Classification Search
CPC .......... A61N 2/00; A61N 2/002; A61N 2/004; A61N 2/006; A61N 2/008; A61N 2/02; A61N 1/3601; A61N 1/40
See application file for complete search history.

(56) References Cited

U.S. PATENT DOCUMENTS

2002/0188332 A1* 12/2002 Lurie ................. A61N 1/39044 607/48
2004/0078056 A1* 4/2004 Zangen .................. A61N 2/006 607/2

(Continued)

FOREIGN PATENT DOCUMENTS

DE 20 2019 100003 U1 2/2019
GB 2587392 A 3/2021

(Continued)

OTHER PUBLICATIONS

International Search Report and Written Opinion issued Jun. 28, 2021 in Intl. Appl. No. PCT/EP2021/059259.

*Primary Examiner* — Carrie R Dorna

(74) *Attorney, Agent, or Firm* — MEDLER FERRO WOODHOUSE & MILLS PLLC

(57) ABSTRACT

A stimulation arrangement is disclosed that includes an induction device having a field generator configured to generate a spatial field having a targeted shape, and a control unit in communication with the induction device and configured to control the induction device to generate the spatial field. The field generator of the induction device is configured to be positioned at a human or animal patient such that, for activating the patient, a target tissue is stimulable by the spatial field generated by the coil design. The control unit is configured to operate the induction device such that the field generator generates a sequence of consecutive trains of plural pulses of the electro-magnetic field, wherein the trains are intermitted.

23 Claims, 2 Drawing Sheets

(56) References Cited

U.S. PATENT DOCUMENTS

| | | | |
|---|---|---|---|
| 2004/0193003 | A1 | 9/2004 | Mechlenburg et al. |
| 2014/0142654 | A1* | 5/2014 | Simon ................ A61N 1/36021 607/46 |
| 2015/0367127 | A1 | 12/2015 | Meyyappan et al. |
| 2022/0362570 | A1 | 11/2022 | Pemberton |

FOREIGN PATENT DOCUMENTS

| | | | |
|---|---|---|---|
| JP | 2015519975 | A1 | 7/2015 |
| WO | 2013188965 | A1 | 12/2013 |
| WO | 2019154839 | A1 | 8/2019 |
| WO | 2021059250 | A1 | 4/2021 |

* cited by examiner

STIMULATION ARRANGEMENT AND METHOD OF ACTIVATING A PATIENT

TECHNICAL FIELD

The present invention relates to a stimulation arrangement according to the preamble of independent claim 1 and more particularly to a process of manufacturing such stimulation arrangement, to a method of activating a patient and to a computer program for controlling an activation of a patient.

BACKGROUND ART

In medicine, it is known that for different therapeutic treatments it is beneficial to activate a patient, i.e., to activate a muscular or similar structure of the patient. Thereby, often it is intended to activate the patient by stimulating a target tissue by means of an electro-magnetic field. For example, in therapeutic applications of knees after surgical interventions it is known to activate the muscles around the knee by direct muscle stimulation via an electro-magnetic field. For such activation, specific stimulation devices are known which can be positioned at the patient and generate the electro-magnetic field.

In another exemplary field, particularly in critical care units of hospitals, it may be desired to activate a diaphragm of a ventilated patient in order to prevent drawbacks of disuse of the diaphragm. For example, it was shown that disuse atrophy of diaphragm muscle fibers occurs already in the first 18-69 hours of mechanical ventilation, and the muscle fiber cross-sections decreased by more than 50% in this time. Thus, it is aimed to activate the diaphragm repeatedly while the patient is given artificially or mechanical respiration such that the functioning of the diaphragm can be upheld, or to activate the diaphragm at least during the weaning period to support effective restoration of independent respiratory function.

For achieving such activation of tissues in a patient's body, as mentioned above, it is known to directly stimulate the tissue or to indirectly activate the tissue via stimulation of specific parts of the neural system. For example, tissue being muscular tissue can be activated by providing electric pulses directly to the tissue or to nerves associated to the tissue. More specifically, it is known that the diaphragm can be activated by stimulating the Phrenic nerve, e.g., at the neck of the patient.

Even though such activation of patients is known, it often induces discomfort to the patient. For example, the sudden provision of electro-magnetic stimulation may cause the body of the patient to induce a reactive response such as sudden convulsion or the like, which may obstruct the therapeutic effect. Also, electro-magnetic stimulation often involves noise generation which may be undesired for the patients' comfort.

Therefore, there is a need for an arrangement, system or procedure allowing a comparably convenient and efficient activation of a patient by stimulation via an electro-magnetic field and, more specifically, allowing an efficient activation of a diaphragm in a ventilation procedure of a patient.

DISCLOSURE OF THE INVENTION

According to the invention this need is settled by a stimulation arrangement as well as by a method of activating a human or animal patient, both as defined by the features of independent claims 20 Preferred embodiments are subject of the dependent claims.

In one aspect, the invention is a stimulation arrangement comprising an induction device and a control unit. The induction device has a field generator configured to generate a spatial field having a targeted shape. The control unit is in communication with the induction device and configured to control the induction device to generate the spatial field. The field generator of the induction device is configured to be positioned at a human or animal patient such that, for activating the patient, a target tissue is stimulable by the spatial field generated by the field generator. The control unit is further configured to operate the induction device such that the field generator generates a sequence of consecutive trains of plural pulses of the spatial field, wherein the trains are intermitted.

Activation of the patient in context of the invention relates to activation of any specific tissue of the body of the patient such as muscle tissue or the like. Thereby, the tissue can be directly activated by stimulating this tissue itself. In such configurations, the tissue to be activated and the target tissue are identical. Alternatively or additionally, the tissue can be indirectly activated such as, in particular, via a portion of the neural system of the patient. The stimulation arrangement can be particularly advantageous for indirectly activating a diaphragm of the patient by stimulating a Phrenic nerve of the patient as target tissue.

The term "spatial field" as in context of the aspects of the invention described below relates to any field allowing stimulation of a target tissue of a patient. It may particularly involve an electric field, a magnetic field or an electro-magnetic field. Such fields allow for directly stimulate muscular structures or indirectly stimulate muscular structures via the nervous system or via other muscular structures.

The targeted shape of the spatial field can be achieved by the spatial field being a locally constrained, e.g., having a peak. It can be adapted to be active in a target area being the nerve area or tissue area that shall be activated with the spatial field (e.g., the phrenic nerve that shall be activated), which can be for example achieved by the peak in the spatial field (focality area). The targeted shape can generally be any shape of the spatial field or time-dependent field component that allows to stimulate one or more target nerves effectively while minimizing other undesired co-stimulation effects of surrounding, above-lying or close-by tissues or nerves. A peak shape is such example, because it maximizes effects in a focality area and minimizes effects outside this area.

The term "pulse" in connection with the invention relates to a comparably short provision of the spatial field. Thereby, single pulses relate to the generation of the spatial field over a comparably short time and with a comparably long interruption between two subsequent pulses. Typically, single pulses are provided at frequencies lower than 10 Hertz (Hz) such as, e.g., at 5 Hz or below, or single pulses are initiated by the user or practitioner. The single pulses can have a temporal width of about 10 microseconds (μs) to about 300 μs. Such pulses can activate nerves and muscle structure and are identifiable by the patient or by a sensor. In particular, such single pulses may cause a single convulsion of a muscle or muscular structure.

In contrast thereto, when being generated as a train rather than in single pulses, the spatial field is either continuously generated or in sequences of pulses comparably quickly following each other. Such pulses can be provided in a frequency range of in between about 15 Hz and about 30 Hz. Each of the plurality of pulses of the trains preferably comprises an essentially identical pulse temporal width which, as mentioned, is comparably short. More specifically, the pulse temporal width preferably is in a range from about 160 microseconds to about 220 microseconds.

In particular, a train may achieve to activate a nerve or muscle such that a tetanic contraction or activation is induced. Advantageously, as described below, the train is provided by increasing the intensity (field strength) and/or frequency until a target intensity and frequency is achieved (ramp protocol). Like this, sudden convulsion or discomfort can be decreased. All of these parameters are summarized under the term "temporal characteristics" or "temporal parameters" of the spatial field. These temporal parameters can be adjusted manually via an input interface or be controlled automatically by an adjustment mechanism or control unit.

Parameters such as the voltage or current waveform applied to generate the spatial field may affect the temporal characteristics of the spatial field, including pulse shape, amplitude, width, polarity, and repetition frequency; duration of and interval between bursts or trains of pulses; total number of pulses; and interval between stimulation sessions and total number of sessions have, amongst others, an influence on the field strength and determine if and with which intensity or "dose" a target area or target tissue can be activated.

The term "train" in context of the invention relates to a sequence of the plural pulses involved. In particular, one single train of the trains typically comprises a group of pulses. Thereby, each of the trains preferably comprises an identical or at least similar number of pulses. In other words, the group of pulses comprised by each single train can consist of the same number of pulses. Further, each of the trains preferably comprises an essentially identical train temporal width. More specifically, the train temporal width preferably is in a range from about 0.5 seconds to about 1.5 seconds. Such pulse trains allow for stimulating the target tissue such that the patient is efficiently activated.

In a preferred embodiment, the field generator of the induction device comprises an electrode and the spatial field generated by the field generator is an electric field.

In an alternative preferred embodiment, the field generator of the induction device comprises a coil design and the spatial field generated by the field generator is an electro-magnetic field. The term "coil design" as used herein can be or comprise at least two coils or at least one cone shaped or otherwise curved or bulged coil, or at least one cylindrical or otherwise non-flat coil, or at least one small coil, i.e., a coil sufficiently small to generate a sharp electro-magnetic field such as a coil having a diameter of 3 cm or less. The targeted shape of the electro-magnetic field described herein can comprise a peak formed by the spatial electro-magnetic field. The electro-magnetic field generator can also be referred to as electro-magnetic field creator.

The coil design of the electro-magnetic field generator allows to shape or customize the electro-magnetic field in compliance with the intended application of the ventilation device. In particular, the targeted shape can be created such that it is comparably sharp. This allows for specifically stimulating the neural system or a specific portion thereof. In particular, it allows for specifically stimulating a nerve such as the Phrenic nerve and for lowering or preventing stimulation of other tissue or nerves neighboring, surrounding or overheading the targeted nerve. In order to stimulate both Phrenic nerves at a neck, the coil design can be provided which is characterized by a double coil generating focal e-field area(s), a parabolic coil or a small circular coil.

The terms "positioned at" or "holding at" as used in connection with field generators of induction devices can relate to a field generator being physically in contact with a body of a patient or in close distance to it. The position and orientation of the field generator or a component of it can thereby be predefined or distinct to be appropriate for stimulating a target tissue. In order to be configured for being positioned at an appropriate location, a field generator can be formed to be suited to the location. Also, it can be equipped with an appropriate mounting structure for being secured at the location.

For a control unit being in communication with any other component, it can be wiredly or wirelessly coupled to the other component. Like this, control signals can be transmitted to the other component for operating or controlling. Additionally or alternatively, signals such as sensor signals can be received by the control unit. For example, such sensor signals may represent a sensed dimension or physical property, e.g., for further evaluation.

The control unit can be any computing entity suitable for performing the tasks involved for controlling the induction device and eventually for other purposes such as data evaluation. It can be or comprise a laptop computer, a desktop computer, a server computer, a tablet, a smartphone or the like. The term "control unit" covers single devices as well as combined devices. The control unit can, for example, be a distributed system, such as a cloud solution, performing different tasks at different locations.

Typically, a control unit or computer involves a processor or central processing unit (CPU), a permanent data storage having a recording media such as a hard disk, a flash memory or the like, a random access memory (RAM), a read only memory (ROM), a communication adapter such as an universal serial bus (USB) adapter, a local area network (LAN) adapter, a wireless LAN (WLAN) adapter, a Bluetooth adapter or the like, and a physical user interface such as a keyboard, a mouse, a touch screen, a screen, a microphone, a speaker or the like. Control units or computers can be embodied with a broad variety of components.

The control unit can be partially or fully embodied as separate component, or as a component integrated in another device or component. For example, the control unit or parts of it can be embodied in a ventilation machine used for ventilating the patient, and/or in the induction device.

Operating the induction device can particularly involve inducing the induction device to apply the spatial field and, thereby, stimulating the target tissue such as a Phrenic nerve or both Phrenic nerves of the patient. Thus, the control unit can activate the diaphragm of the patient by operating the induction device.

By operating the induction device such that a sequence of consecutive intermitted trains is generated, the stimulation can be sophisticatedly adapted and adjusted in accordance with the needs and requirements given in a specific therapy. For example, such configuration allows for integrating stimulation of the activation of the diaphragm in a conventional ventilation application. Like this, the ventilation can conveniently be supported by the stimulation arrangements and downsides of pure mechanical ventilation can be reduced. Thus, the stimulation arrangement according to the invention allows for a comparably convenient and efficient activation of the patient.

Preferably, the plural pulses of each of the trains comprise a first pulse having a first intensity and a maximum pulse having a maximum intensity, wherein the maximum intensity is higher than the first intensity. The first pulse in this connection is the first pulse of the respective train of pulses. The maximum pulse may be the last pulse of the respective train or any pulse after the first pulse of the train. Further, there can be plural pulses having the maximum intensity in the one single train.

The term “intensity” as used in connection with one of the pulses relates to a field strength of the spatial field being created in the respective pulse. The field strength typically means a magnitude of a vector-valued field, which can be measured in volts per meter for an electric field and in ampere per meter for a magnetic field. Provision of an electro-magnetic field as spatial field results in both electric field strength and magnetic field strength. However, in the electro-magnetic field one of the electric field strength or the magnetic field strength may be negligible.

The intensities of intermediate pulses between the first pulse and the maximum pulse preferably raise from the first pulse to the maximum pulse. Such configuration of the trains allows for increasing convenience for the patient. In particular, by having a lower intensity at the beginning each train may achieve to condition the patient by a comparably smooth start. Such smooth start may be comparable to a natural movement of the tissue to be activated. Like this, sudden convulsion and discomfort can be prevented and the efficacy of the activation can be increased.

Additionally or alternatively, the plural pulses of each of the trains preferably comprise a last pulse having a last intensity, wherein the last intensity is lower than the maximum intensity. The first and the last intensity may the same. Thereby, the intensities of intermediate pulses between the maximum pulse and the last pulse preferably lower from the maximum pulse to the last pulse. By reducing the intensity in each train towards an end of the train, the tissue, e.g., the diaphragm, of the patient can more naturally be activated such that comfort can be further increased.

As mentioned above, each single pulse of the plural pulses typically has a pulse temporal width, wherein the pulse temporal width can be essentially the same for all pulses. Preferably, the pulse temporal width comprises an increasing portion, in which the intensity is increased, and/or a decreasing portion, in which the intensity is decreased. In case the spatial field is an electro-magnetic field, since during the pulses comparably large electro-magnetic forces between the windings of coils of the electro-magnetic field generator may be involved which forces have an effect on the coils comparable to an impact with a baton, noise can be produced. Such noise can lead to discomfort for the patient and the surrounding. However, by providing the single pulses with an increasing portion and/or a decreasing portion the final intensity can be increasingly established and reduced. Like this, the noise induced by single pulses can essentially be reduced. This allows for increasing comfort during activation of the patient.

The increasing portion and the decreasing portion of one single pulse can be established by providing plural sub-pulses of varying intensity. Such sub-pulses can particularly be high frequency sub pulses. More specifically, the increasing portion of one single pulse can be established by plural sub-pulses having increasing intensities. Vice versa, the decreasing portion of one single pulse can be established by plural sub-pulses having decreasing intensities.

To achieve a noise reduction to a satisfying extent, the increasing portion and particularly the decreasing portion together preferably cover at least 60 percent of the pulse temporal width or at least 80 percent of the pulse temporal width. In particular, the intensity of each single pulse can describe a clock-like shape.

Preferably, each of the trains comprises an accumulated intensity calculated by summarizing the intensities of its pulses, wherein the accumulated intensities of the trains differ. There might also be trains having the same accumulated intensity. However, in general, the accumulated intensities of at least two or, advantageously, more of the trains vary.

Thereby, the trains preferably comprise a first train having a first accumulated intensity and a maximum train having a maximum accumulated intensity, wherein the maximum accumulated intensity is higher than the first accumulated intensity. More specifically, the trains can have plural increasing trains in which the accumulated intensity is increased from the first accumulated intensity to the maximum accumulated intensity. By increasing the accumulated intensity from the first accumulated intensity to the maximum accumulated intensity, advantageously by stepwise increasing the accumulated intensity from one train to a subsequent train, a comparably high accumulated intensity can be provided to the patient without causing discomfort. Rather, the patient can be conditioned to the maximum accumulated intensity. This allows for providing an efficient activation involving comparably high intensities without essential discomfort or counter reaction such as sudden convulsion.

Preferably, each of the trains comprises an identical number of pulses. Additionally or alternatively, each of the trains preferably comprises an essentially identical train temporal width. Thereby, the train temporal width preferably is in a range from about 0.5 seconds to about 1.5 seconds. Such configuration allows for providing a steady stimulation which may decrease discomfort or surprise of the patient causing a counter reaction such as sudden convulsion.

Preferably, the trains comprise about ten to about twenty trains per minute. Such frequency of the trains has proven to provide for an efficient stimulation of the target tissue und, thus, an efficient activation of the patient in a comfortable manner.

Furthermore, the plurality of pulses of the trains preferably comprises a frequency in a range from about 15 Hertz to about 25 Hertz. Providing the pulses at such frequency allows for achieving an efficient stimulation. A combination of the above train frequency with this pulse frequency can be particularly beneficial.

In another aspect, the invention is a process of manufacturing a stimulation arrangement. This manufacturing process comprises the steps of (i) providing an induction device having a field generator configured to generate a spatial field having a targeted shape, (ii) configuring the induction device to be positioned at a human or animal patient such that, for activating the patient, a target tissue is stimulable by the spatial field generated by the coil design, (iii) providing a control unit adapted to be in communication with the induction device, (iv) configuring the control unit to control the induction device to generate the spatial field, and (v) configuring the control unit to operate the induction device such that the field generator generates a sequence of consecutive trains of plural pulses of the spatial field, wherein the trains are intermitted.

The manufacturing process according to the invention allows for providing the stimulation arrangement according to the invention described above. Like this, the effects and benefits described above in connection with the stimulation arrangement can efficiently be achieved. Furthermore, the effects and benefits described above in connection with the preferred features of the stimulation arrangement can be achieved by the following additional steps and features of the manufacturing process:

Preferred step of: Configuring the control unit to operate the induction device such that the field generator generates the plural pulses of each of the trains with a first pulse having a first intensity and a maximum pulse having a maximum intensity, wherein the maximum intensity is higher than the first intensity. Thereby, the intensities of intermediate pulses between the first pulse and the maximum pulse can raise from the first pulse to the maximum pulse. Further. the plural pulses of each of the trains can comprise a last pulse having a last intensity, wherein the last intensity is lower than the maximum intensity, wherein the intensities of intermediate pulses between the maximum pulse and the last pulse can lower from the maximum pulse to the last pulse.

Preferred step of: Configuring the control unit to operate the induction device such that the field generator generates each of the trains with an accumulated intensity calculated by summarizing the intensities of its pulses, wherein the accumulated intensities of the trains differ. Thereby, the trains can comprise a first train having a first accumulated intensity and a maximum train having a maximum accumulated intensity, wherein the maximum accumulated intensity is higher than the first accumulated intensity.

Preferred step of: Configuring the control unit to operate the induction device such that the field generator generates each of the trains with an identical number of pulses.

Preferred step of: Configuring the control unit to operate the induction device such that the field generator generates each of the trains with an essentially identical train temporal width. Thereby, the train temporal width can be in a range from about 0.5 seconds to about 1.5 seconds.

Preferred step of: Configuring the control unit to operate the induction device such that the field generator generates the trains with about ten to about twenty trains per minute.

Preferred step of: Configuring the control unit to operate the induction device such that the field generator generates each of the plurality of pulses of the trains with an essentially identical pulse temporal width. Thereby, the pulse temporal width can be in a range from about 160 microseconds to about 220 microseconds. Further, the pulse temporal width can comprise an increasing portion, in which the intensity is increased, and/or a decreasing portion, in which the intensity is decreased, wherein the increasing portion and the decreasing portion together preferably cover at least 60 percent of the pulse temporal width.

Preferred step of: Configuring the control unit to operate the induction device such that the field generator generates the plurality of pulses of the trains with a frequency in a range from about 15 Hertz to about 25 Hertz.

In a preferred embodiment, the field generator of the induction device provided comprises an electrode and the spatial field generated by the field generator is an electric field.

In another preferred embodiment, the field generator of the induction device provided comprises a coil design and the spatial field generated by the field generator is an electro-magnetic field.

In a further other aspect, the invention is a method of activating a human or animal patient by stimulating a target tissue of the patient. This activation method comprises the steps of (a) obtaining an induction device having a field generator configured to generate a spatial field having a targeted shape and a control unit which is in communication with the induction device and which is configured to control the induction device to generate the spatial field, (b) positioning the field generator of the induction device at the patient such that the target tissue is stimulable by the spatial field generated by the coil design, and (c) operating the induction device such that the field generator generates a sequence of consecutive trains of plural pulses of the spatial field, wherein the trains are intermitted.

The activation method according to the invention allows for efficiently achieving the effects and benefits described above in connection with the stimulation arrangement. Thereby, advantageously such stimulation arrangement is used for applying the activation method or at least some portions thereof.

Preferably, the target tissue is a Phrenic nerve of the patient and activating the patient is activating a diaphragm of the patient. Like this, the method can be used for ventilating or assisting ventilation of the patient. In such applications the invention may be particularly beneficial.

More specifically, the activation method preferably comprises the steps of connecting a conduit interface to a respiratory system of the patient, delivering air through the conduit interface into the respiratory system of the patient, controlling the delivery of air into the respiratory system of the patient according to a breathing scheme, and activating the diaphragm of the patient in coordination with the breathing scheme. Such implementation of the activation method may provide for efficient assistance of mechanical ventilation and to prevent or reduce the risk of side effects like developing an acute respiratory distress syndrome (ARDS) or ventilator associated pneumonia (VAP) or ventilator-induced lung injury (VILI).

By the following additional steps and features of the activation method the effects and benefits described above in connection with the preferred features of the stimulation arrangement can be achieved by the following additional steps and features of the activation method:

Preferably, the plural pulses of each of the trains generated by the field generator of the induction device comprise a first pulse having a first intensity and a maximum pulse having a maximum intensity, wherein the maximum intensity is higher than the first intensity. Thereby, the intensities of intermediate pulses between the first pulse and the maximum pulse preferably raise from the first pulse to the maximum pulse. Furthermore, the plural pulses of each of the trains preferably comprise a last pulse having a last intensity, wherein the last intensity is lower than the maximum intensity, wherein the intensities of intermediate pulses between the maximum pulse and the last pulse preferably lower from the maximum pulse to the last pulse.

Preferably, each of the trains comprises an accumulated intensity calculated by summarizing the intensities of its pulses, wherein the accumulated intensities of the trains are different. Thereby, each of the trains preferably comprises a first train having a first accumulated intensity and a maximum train having a maximum accumulated intensity, wherein the maximum accumulated intensity is higher than the first accumulated intensity.

Preferably, each of the trains comprises an identical number of pulses.

Preferably, each of the trains comprises an essentially identical train temporal width. Thereby, the train temporal width preferably is in a range from about 0.5 seconds to about 1.5 seconds.

Preferably, the trains comprise about ten to about twenty trains per minute.

Preferably, each of the plurality of pulses of the trains comprises an essentially identical pulse temporal width. Thereby, the pulse temporal width preferably is in a range from about 160 microseconds to about 220 microseconds. Furthermore, the pulse temporal width preferably comprises an increasing portion, in which the intensity is increased, and/or a decreasing portion, in which the intensity is decreased, wherein the increasing portion and the decreasing portion together preferably cover at least 60 percent of the pulse temporal width.

Preferably, the plurality of pulses of the trains comprises a frequency in a range from about 15 Hertz to about 25 Hertz.

In a preferred embodiment, the field generator of the induction device used in the method comprises an electrode and the spatial field generated by the field generator is an electric field.

In another preferred embodiment, the field generator of the induction device used in the method comprises a coil design and the spatial field generated by the field generator is an electro-magnetic field.

In still a further other aspect, the invention is a computer program comprising instructions which, when the program is executed by a control unit, cause the control unit to operate a field generator of an induction device positioned at a human or animal patient such that a target tissue of the patient is stimulable by a spatial field generated by a the coil design of the field generator of the induction device, such that the field generator generates a sequence of consecutive trains of plural pulses of the spatial field, wherein the trains are intermitted.

The computer program can be a computer program product comprising computer code means configured to control a processor of a computer to implement the steps and/or features described above or below when being executed on the control unit. Further, there can be provided a computer-readable medium comprising instructions which, when executed by a computer or control unit, cause the computer or control unit to carry out the steps and/or features described above or below. The medium can a storage medium and, for allowing a convenient distribution, a mobile or portable storage medium. Or, for allowing a transfer over the Internet or the like, or for other purposes, there can be provided a data carrier signal carrying the computer program described herein before. The computer program can also be referred to as or comprised by a software.

The computer program according to the invention allows for efficiently achieving the effects and benefits described above in connection with the stimulation arrangement. Thereby, advantageously such stimulation arrangement or at least some parts thereof such as its control unit is involved for executing the computer program.

In the following advantageous embodiments of the computer program according to the invention are described which allow to achieve the effects and benefits described above in connection with the preferred embodiments of the stimulation arrangement.

Preferably, the plural pulses of each of the trains comprise a first pulse having a first intensity and a maximum pulse having a maximum intensity, wherein the maximum intensity is higher than the first intensity. Thereby, the intensities of intermediate pulses between the first pulse and the maximum pulse preferably raise from the first pulse to the maximum pulse. Further, the plural pulses of each of the trains preferably comprise a last pulse having a last intensity, wherein the last intensity is lower than the maximum intensity, wherein the intensities of intermediate pulses between the maximum pulse and the last pulse preferably lower from the maximum pulse to the last pulse.

Preferably, each of the trains comprises an accumulated intensity calculated by summarizing the intensities of its pulses, wherein the accumulated intensities of the trains differ. Thereby, each of the trains preferably comprises a first train having a first accumulated intensity and a maximum train having a maximum accumulated intensity, wherein the maximum accumulated intensity is higher than the first accumulated intensity.

Preferably, each of the trains comprises an identical number of pulses.

Preferably, each of the trains comprises an essentially identical train temporal width. Thereby, the train temporal width preferably is in a range from about 0.5 seconds to about 1.5 seconds.

Preferably, the trains comprise about ten to about twenty trains per minute.

Preferably, each of the plurality of pulses of the trains comprises an essentially identical pulse temporal width. Thereby, the pulse temporal width preferably is in a range from about 160 microseconds to about 220 microseconds. Further, the pulse temporal width preferably comprises an increasing portion, in which the intensity is increased, and a decreasing portion, in which the intensity is decreased, wherein the increasing portion and the decreasing portion together preferably cover at least 60 percent of the pulse temporal width.

Preferably, the plurality of pulses of the trains comprises a frequency in a range from about 15 Hertz to about 25 Hertz.

In preferred embodiment of the computer program, the field generator of the induction device comprises an electrode and the spatial field generated by the field generator is an electric field.

In another preferred embodiment of the computer program, the field generator of the induction device comprises a coil design and the spatial field generated by the field generator is an electro-magnetic field.

BRIEF DESCRIPTION OF THE DRAWINGS

The stimulation arrangement according to the invention, the process of manufacturing such stimulation arrangement according to the invention, the method of activating a patient according to the invention and the computer program for controlling an activation of a patient according to the invention are described in more detail herein below by way of exemplary embodiments and with reference to the attached drawings, in which.

DESCRIPTION OF EMBODIMENTS

In the following description certain terms are used for reasons of convenience and are not intended to limit the invention. The terms “right”, “left”, “up”, “down”, “under” and “above” refer to directions in the figures. The terminology comprises the explicitly mentioned terms as well as their derivations and terms with a similar meaning. Also, spatially relative terms, such as “beneath”, “below”, "lower", "above", "upper", "proximal", "distal", and the like, may be used to describe one element's or feature's relationship to another element or feature as illustrated in the figures. These spatially relative terms are intended to encompass different positions and orientations of the devices in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. The devices may be otherwise oriented (rotated 90 degrees or at other orientations), and the spatially relative descriptors used herein interpreted accordingly. Likewise, descriptions of movement along and around various axes include various special device positions and orientations.

To avoid repetition in the figures and the descriptions of the various aspects and illustrative embodiments, it should be understood that many features are common to many aspects and embodiments. Omission of an aspect from a description or figure does not imply that the aspect is missing from embodiments that incorporate that aspect. Instead, the aspect may have been omitted for clarity and to avoid prolix description. In this context, the following applies to the rest of this description: If, in order to clarify the drawings, a figure contains reference signs which are not explained in the directly associated part of the description, then it is referred to previous or following description sections. Further, for reason of lucidity, if in a drawing not all features of a part are provided with reference signs it is referred to other drawings showing the same part. Like numbers in two or more figures represent the same or similar elements.

Figure 1:
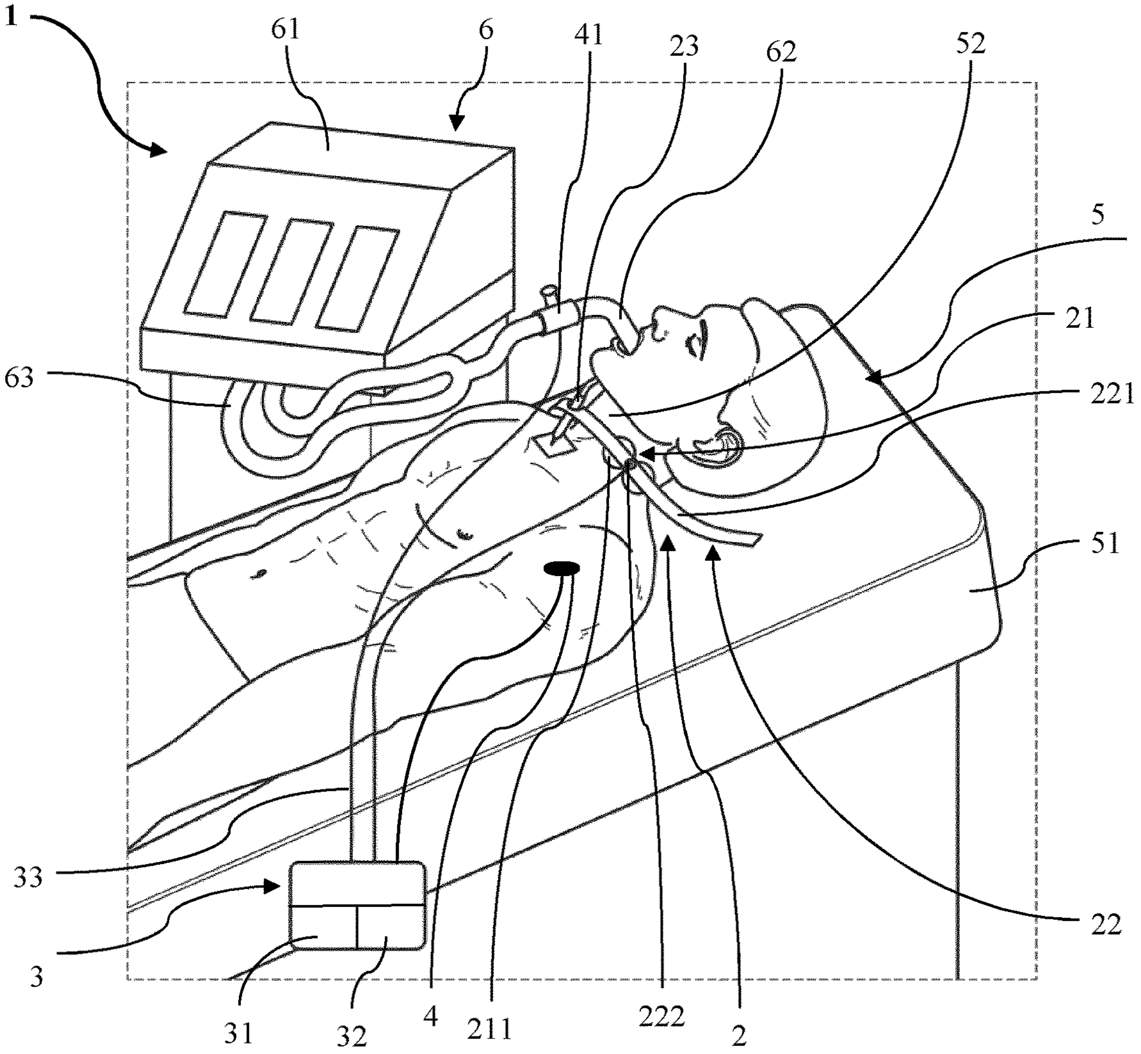
FIG. 1 shows a schematic view of an embodiment of a stimulation arrangement according to the invention embodied in a ventilation arrangement, manufactured by a process according to the invention, implementing an embodiment of a method according to the invention, and running a computer program according to the invention.

FIG. 1 shows an embodiment of a stimulation arrangement 1 according to the invention embodied as a ventilation arrangement. The stimulation arrangement 1 includes a ventilation machine 6, an electro-magnetic induction device 2 (in the following also referred to as EMI device) as induction device, a control unit 3 and a sensor 4. The EMI device 2 comprises an electro-magnetic field generator 21 as field generator with two coils 211 as coil design. The coils 211 are located in one common plane and configured to generate a spatial electro-magnetic field 212 as spatial field. When operated, the two coils 211 generate the electro-magnetic field towards a neck 52 of a patient 5. The electro-magnetic field has a central targeted shape with a focality area at which the electro-magnetic field maximally extends into the neck 52. Further, the EMI device 2 has a mounting arrangement 22 with a neck arc 221 arranged at the neck 52 of the patient 5 and fixed to a bed 51 on which the patient 5 lies. The neck arc 221 is equipped with a joint 222 as repositioning structure of an electro-magnetic field adjustment mechanism of the EMI device 2. The joint 222 holds the coils 211 at the neck 52 of the patient 5.

The ventilation machine 6 comprises a ventilator 61 as air flow generator from which ventilation tubes 63 extend, and a mouthpiece 62 as conduit interface. The mouthpiece 62 is a tube provided through a mouth of the patient into the respiratory system of the patient 5.

The control unit 3 has a user interface 31 for exchanging information with a practitioner supervising or setting up ventilation of the patient 5. For example, the user interface 31 can be embodied as touch screen allowing to in- and output information. Further, the control unit 3 is equipped with a device interface 32 arranged to be coupled to an interface unit of the ventilation machine 6, the EMI device 2 and the sensor 4 by wires 33. Like this, the control unit 3 is in communication with the ventilation machine 6, the EMI device 2 and the sensor 4.

More specifically, the control unit 3 is configured to receive ventilation data about the ventilation of the patient 5 from the ventilation machine 6 and to control the EMI device 2 to generate the spatial electro-magnetic field in accordance with the evaluated ventilation data as described in more detail below. Furthermore, the control unit 3 is configured to manipulate the joint 222 to automatically vary the position of the focality area 213 of the spatial electro-magnetic field 212 generated by the coils 211 and to vary the field strength of the spatial electro-magnetic field 212. The aim of varying field strength and position of the spatial electro-magnetic field 212 is to adjust the spatial electro-magnetic field 212 such that it specifically stimulates a Phrenic nerve of the patient 5. Upon stimulation of the Phrenic nerve 53, a diaphragm of the patient 5 is activated. Thereby, an airflow or breathing is induced.

The ventilation machine 6 is configured to mechanically ventilate the patient 5 by advancing air through the mouthpiece 62 into the respiratory system of the patient 5. More specifically, the ventilator 61 is configured to deliver the air through the mouthpiece 62. The control unit 3 is configured to control the ventilator 61 to deliver the air according to a breathing scheme defined in the control unit 3. Moreover, the control unit 3 regulates the activation of the diaphragm in coordination with the breathing scheme such that activation of the diaphragm via the Phrenic nerve 53 is coordinated with the ventilation of the patient 5.

For being able to provide various treatments during ventilation, the control unit 3 has a computer which executes a computer program configuring the control unit 3 to define combinations of a stimulation duration and a repetition rate, and to operate the EMI device 2 in accordance with the defined stimulation duration and the determined repetition rate. Thereby, the control unit 3 provides a selection of treatments to the practitioner via the user interface 31. The practitioner selects an appropriate treatment and sets parameters involved.

For allowing prevention of diaphragm muscle loss and/or reduction of risk of VIDD, a first operation mode is set in the control unit 3 by defining the stimulation duration to be in a range of about 3 minutes to about 20 minutes and the repetition rate to be in a range of about once per day to about 3 times per day.

For allowing reduction of a risk of developing an ARDS, a second operation mode is set in the control unit 3 by defining the repetition rate to be in a range of about twice per hour to about every two hours and the stimulation duration to be in a range of about 0.5 minutes to about 3 minutes.

For alternatively allowing reduction of the risk of developing ARDS, a third operation mode is set in the control unit 3 by defining the stimulation duration to be in a range of about 1 breathing cycle to about 5 breathing cycles and the repetition rate to be in a range of about every minute to about every 30 minutes.

For inducing breathing cycles or stimulating deep breathing, a fourth operation mode is set in the control unit 3. In this fourth operation mode, the control unit 3 evaluates an oxygen level or a carbon dioxide level in the blood of the patient 5 measured by the sensor 4 and compares it to a predefined threshold. The control unit 3 then operates the EMI device 2 when the measured oxygen level or carbon dioxide level bypasses the predefined threshold. In particular, it operates the EMI device 2 when the measured oxygen level is below the threshold or when the measured carbon dioxide level is above the threshold.

Moreover, by executing the computer program the control unit 3 is configured to operate the EMI device 2 such that the electro-magnetic field generator 21 generates a sequence of consecutive trains of plural pulses of the spatial electro-magnetic field, wherein the trains are intermitted.

Figure 2:
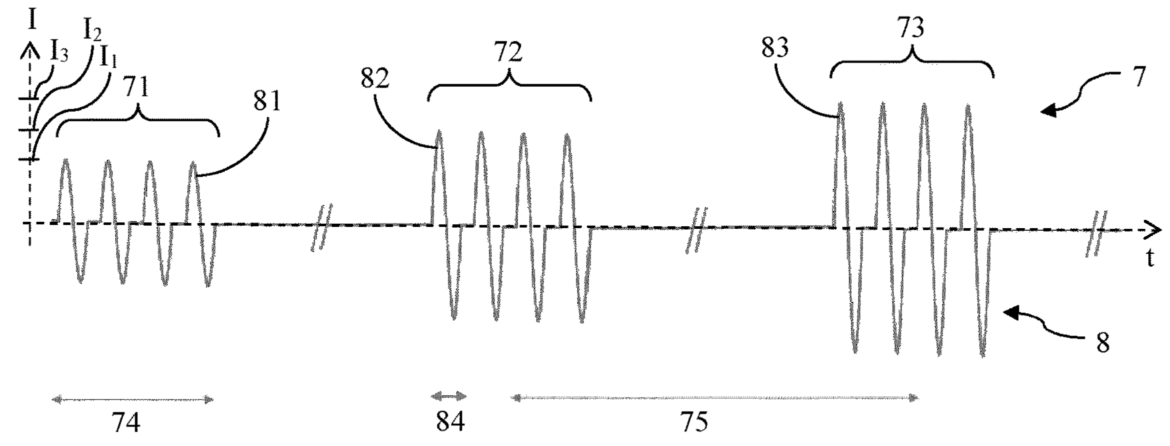
FIG. 2 shows a first embodiment of electro-magnetic field train provision in accordance with the invention.

As shown in FIG. 2 in a first embodiment, the control unit 3 operates the EMI device 2 such that the electro-magnetic field generator 21 generates the sequence of trains 7, wherein each train 7 comprises a group of four electro-magnetic field pulses 8 having a pulse temporal width 84 of 160 microseconds (μs). The trains 7 have a uniform train temporal width 74 of 0.5 second (s). The trains 7 are intermitted by a uniform break of between 2 s and 5 s.

The single pulses 8 of each train 7 have an identical intensity I. More specifically, a first train 71 comprises four first pulses 81 having a first intensity $I_1$, a second train 72 comprises four second pulses 82 having a second intensity 12 and a third maximum train 73 comprises four pulses 83 having a third maximum intensity 13. Each of the trains 7 comprises an accumulated intensity calculated by summarizing the intensities of its pulses 7. Thereby, a first accumulated intensity of the first train 71 is calculated by summarizing the four first intensities $I_1$ of its first pulses 81. Correspondingly, a second accumulated intensity of the second train 72 is calculated by summarizing the four second intensities $I_2$ of its second pulses 82 and a maximum accumulated intensity of the maximum train 73 is calculated by summarizing the four maximum intensities $I_3$ of its maximum pulses 83. Thus, the accumulated intensities of the trains 7 differ by the first accumulated intensity of the first train 71 being lower than the second accumulated intensity of the second train 72 being lower than the maximum accumulated intensity of the maximum train 73.

By stepwise raising the accumulated intensity from one train 7 to the next one, the patient 5 is accommodated to the maximum accumulated intensity. Like this, acceptance can be increased and counter reactions of the patient 5 can be prevented.

Figure 3:
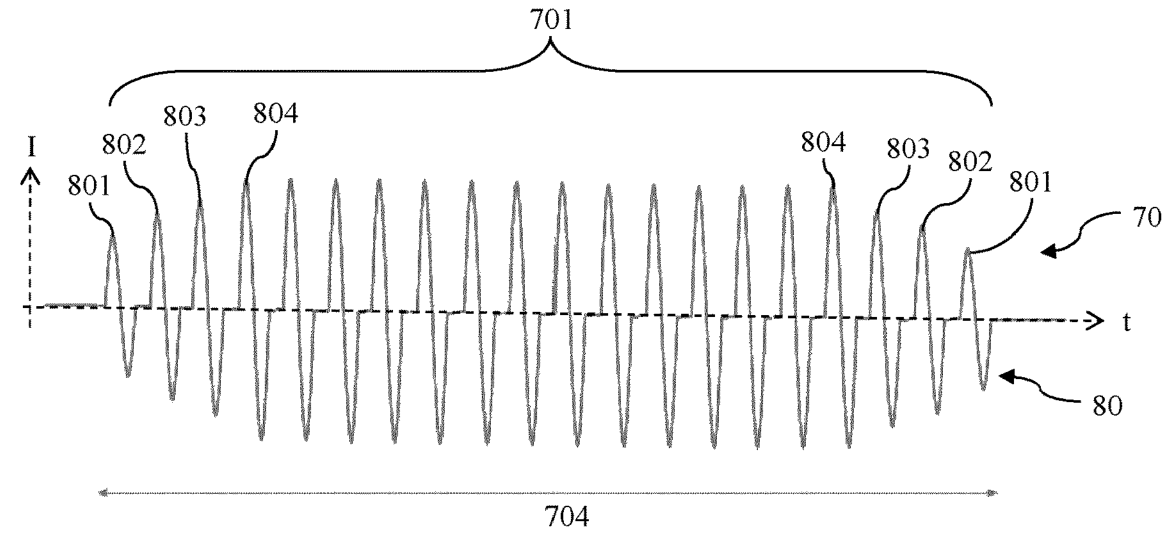
FIG. 3 shows a second embodiment of electro-magnetic field train provision in accordance with the invention.

As shown in FIG. 3, in a second embodiment the control unit 3 operates the EMI device 2 such that the electro-magnetic field generator 21 generates trains 70, wherein each train 701 comprises a group of twenty electro-magnetic field pulses. In particular, the train 70 comprises a first pulse 801 having a first intensity followed by a second pulse 802 having a second intensity, which is higher than the first intensity, followed by a third pulse 803 having a third intensity, which is higher than the second intensity, followed by fourteen maximum pulses 804 having a maximum intensity, which is higher than the third intensity, followed by another third pulse 803 followed by another second pulse 802 followed by another first pulse 801. The train 701 has a train temporal width of 1 s.

By stepwise raising the intensity within each single train 701 from the first pulse 801 over the second pulse 802 and the third pulse 803 to the maximum pulse 804, the patient 5 is accommodated to the maximum intensity. Like this, acceptance of each train 701 can be increased and counter reactions of the patient 5 such as sudden convulsion can be prevented.

Figure 4:
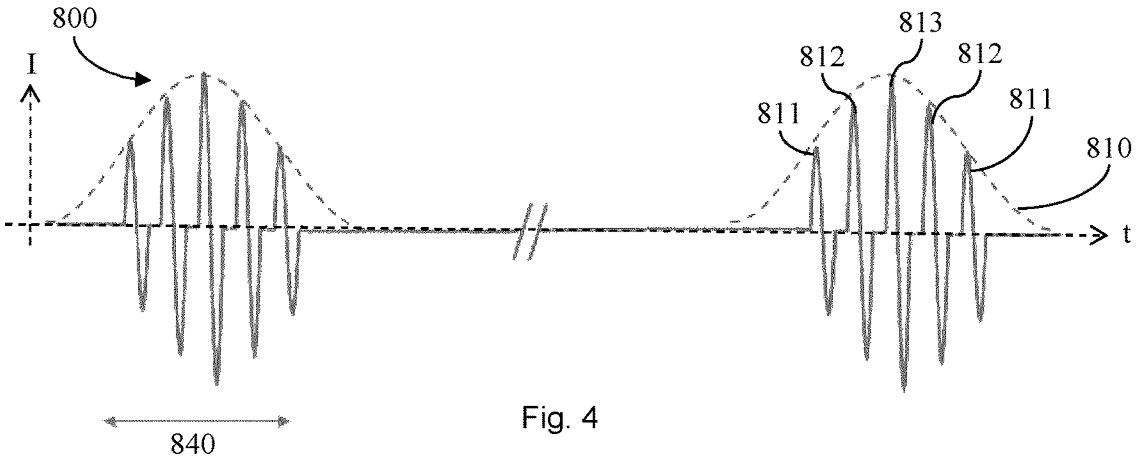
FIG. 4 shows single pulses of a third embodiment of electro-magnetic field train provision.

As shown in FIG. 4, in a third embodiment the control unit 3 operates the EMI device 2 such that the electro-magnetic field generator 21 generates single pulses 800 comprising high frequency sub-pulses. Each pulse 800 comprises a group of five electro-magnetic field sub-pulses. More specifically, each pulse comprises a first sub-pulse 811 having a first intensity followed by a second sub-pulse 812 having a second intensity, which is higher than the first intensity, followed by a sub-third pulse 813 having a third intensity, which is higher than the second intensity, followed by a maximum sub-pulses 814 having a maximum intensity, which is higher than the third intensity, followed by another third sub-pulse 813 followed by another second sub-pulse 812 followed by another first sub-pulse 801. The sub-pulses generate a bell like shaped intensity 810 of the pulse. Each of the pulses has a pulse temporal width 840 of 160 μs. The first, second and maximum sub-pulses 811, 812, 813 at the beginning of the pulse 800 form an increasing portion of the pulse 800. The third, second and first sub pulses 813, 812, 822 at the end of the pulse 800 form a decreasing portion of the pulse 800.

By raising the intensity within each single pulse 800 in its increasing portion from the first sub-pulse 811 over the second sub-pulse 812 and the third sub-pulse 813 to the maximum sub-pulse 814, the patient 5 is accommodated to the intensity of each single pulse. Like this, acceptance of each pulse 800 can be increased such that higher pulse intensities can be provided. Furthermore, by additionally lowering the intensity within each single pulse 800 in its decreasing portion from the maximum sub-pulse 814 over the third sub-pulse 813 and the second sub-pulse 812 to the first sub-pulse 811, the generation of noise can be essentially decreased. Like this, acceptance of the stimulation therapy can be further increased.

This description and the accompanying drawings that illustrate aspects and embodiments of the present invention should not be taken as limiting-the claims defining the protected invention. In other words, while the invention has been illustrated and described in detail in the drawings and foregoing description, such illustration and description are to be considered illustrative or exemplary and not restrictive. Various mechanical, compositional, structural, electrical, and operational changes may be made without departing from the spirit and scope of this description and the claims. In some instances, well-known circuits, structures and techniques have not been shown in detail in order not to obscure the invention. Thus, it will be understood that changes and modifications may be made by those of ordinary skill within the scope and spirit of the following claims. In particular, the present invention covers further embodiments with any combination of features from different embodiments described above and below. For example, it is possible to operate the invention in embodiments where

- pulse provision within single trains as shown in FIG. 3 is combined with the adaptation of the accumulated intensities of trains as shown in FIG. 2, and/or
- pulse provision with clock- or similar shaped pulse intensities as shown FIG. 4 is combined with pulse provision within single trains as shown in FIG. 3 and/or with the adaptation of the accumulated intensities of trains as shown in FIG. 2.

The disclosure also covers all further features shown in the FIGS. individually although they may not have been described in the afore or following description. Also, single alternatives of the embodiments described in the figures and the description and single alternatives of features thereof can be disclaimed from the subject matter of the invention or from disclosed subject matter. The disclosure comprises subject matter consisting of the features defined in the claims or the exemplary embodiments as well as subject matter comprising said features.

Furthermore, in the claims the word "comprising" does not exclude other elements or steps, and the indefinite article "a" or "an" does not exclude a plurality. A single unit or step may fulfil the functions of several features recited in the claims. The mere fact that certain measures are recited in mutually different dependent claims does not indicate that a combination of these measures cannot be used to advantage. The terms "essentially", "about", "approximately" and the like in connection with an attribute or a value particularly also define exactly the attribute or exactly the value, respectively. The term "about" in the context of a given numerate value or range refers to a value or range that is, e.g., within 20%, within 10%, within 5%, or within 2% of the given value or range. Components described as coupled or connected may be electrically or mechanically directly coupled, or they may be indirectly coupled via one or more intermediate components. Any reference signs in the claims should not be construed as limiting the scope.

A computer program may be stored/distributed on a suitable medium, such as an optical storage medium or a solid-state medium supplied together with or as part of other hardware, but may also be distributed in other forms, such as via the Internet or other wired or wireless telecommunication systems. In particular, e.g., a computer program can be a computer program product stored on a computer readable medium which computer program product can have computer executable program code adapted to be executed to implement a specific method such as the method according to the invention. Furthermore, a computer program can also be a data structure product or a signal for embodying a specific method such as the method according to the invention.

The invention claimed is:

1. A stimulation arrangement comprising an induction device having a field generator configured to generate a spatial field having a targeted shape; and a controller in communication with the induction device and configured to control the induction device to generate the spatial field, wherein the field generator of the induction device is configured to be positioned at a human or animal patient such that, for activating the patient, a target tissue is stimulable by the spatial field generated by the field generator, wherein the controller is configured to operate the induction device such that the field generator generates a sequence of consecutive trains of plural pulses of the spatial field, wherein the trains are intermitted and wherein each of the trains comprises an accumulated intensity calculated by summarizing the intensities of its pulses, wherein the accumulated intensities of the trains differ.

2. The stimulation arrangement of claim 1, wherein the plural pulses of each of the trains comprise a first pulse having a first intensity and a maximum pulse having a maximum intensity, wherein the maximum intensity is higher than the first intensity, or wherein the plural pulses of each of the trains comprise a first pulse having a first intensity and a maximum pulse having a maximum intensity, wherein the maximum intensity is higher than the first intensity, wherein the intensities of intermediate pulses between the first pulse and the maximum pulse raise from the first pulse to the maximum pulse.

3. The stimulation arrangement of claim 2, wherein the plural pulses of each of the trains comprise a last pulse having a last intensity, wherein the last intensity is lower than the maximum intensity, wherein the intensities of intermediate pulses between the maximum pulse, or wherein the plural pulses of each of the trains comprise a last pulse having a last intensity, wherein the last intensity is lower than the maximum intensity, wherein the intensities of intermediate pulses between the maximum pulse and the last pulse lower from the maximum pulse to the last pulse.

4. The stimulation arrangement of claim 1, wherein the trains comprise a first train having a first accumulated intensity and a maximum train having a maximum accumulated intensity, the maximum accumulated intensity being higher than the first accumulated intensity.

5. The stimulation arrangement of claim 1, wherein each of the trains comprises an identical number of pulses, and/or an essentially identical train temporal width, or wherein each of the trains comprises an identical number of pulses, and/or an essentially identical train temporal width and wherein the train temporal width is in a range from about 0.5 seconds to about 1.5 seconds.

6. The stimulation arrangement of claim 1, wherein the trains comprise about ten to about twenty trains per minute.

7. The stimulation arrangement of claim 1, wherein each of the plural pulses of the trains comprises an essentially identical pulse temporal width, or wherein each of the plural pulses of the trains comprises an essentially identical pulse temporal width and wherein the pulse temporal width is in a range from about 160 microseconds to about 220 microseconds.

8. The stimulation arrangement of claim 7, wherein the pulse temporal width comprises an increasing portion, in which the intensity is increased, and/or a decreasing portion, in which the intensity is decreased.

9. The stimulation arrangement of claim 7, wherein the pulse temporal width comprises an increasing portion, in which the intensity is increased, and a decreasing portion, in which the intensity is decreased, and wherein the increasing portion and the decreasing portion together cover at least 60 percent of the pulse temporal width.

10. The stimulation arrangement of claim 1, wherein the plural pulses of the trains comprise a frequency in a range from about 15 Hertz to about 25 Hertz.

11. The stimulation arrangement of claim 1, wherein the field generator of the induction device comprises an electrode and the spatial field generated by the field generator is an electric field, or a coil design and the spatial field generated by the field generator is an electro-magnetic field.

12. A method of activating a human or animal patient by stimulating a target tissue of the patient, comprising:

obtaining an induction device having a field generator configured to generate a spatial field having a targeted shape and a controller that is in communication with the induction device and which is configured to control the induction device to generate the spatial field;

positioning the field generator of the induction device at the patient such that the target tissue is stimulable by the spatial field generated by the field generator; and operating the induction device such that the field generator generates a sequence of consecutive trains of plural pulses of the spatial field, wherein the trains are intermitted, wherein each of the trains comprises an accumulated intensity calculated by summarizing the intensities of its pulses, wherein the accumulated intensities of the trains are different.

13. The method of claim 12, wherein the target tissue is a Phrenic nerve of the patient and activating the patient is activating a diaphragm of the patient, wherein the method further comprises:

connecting a conduit interface to a respiratory system of the patient;

delivering air through the conduit interface into the respiratory system of the patient;

controlling the delivery of air into the respiratory system of the patient according to a breathing scheme; and activating the diaphragm of the patient in coordination with the breathing scheme.

14. The method of claim 12, wherein the plural pulses of each of the trains generated by the field generator of the induction device comprise a first pulse having a first intensity and a maximum pulse having a maximum intensity, wherein the maximum intensity is higher than the first intensity, or wherein the plural pulses of each of the trains generated by the field generator of the induction device comprise a first pulse having a first intensity and a maximum pulse having a maximum intensity, wherein the maximum intensity is higher than the first intensity and wherein the intensities of intermediate pulses between the first pulse and the maximum pulse raise from the first pulse to the maximum pulse.

15. The method of claim 14, wherein the plural pulses of each of the trains comprise a last pulse having a last intensity, wherein the last intensity is lower than the maximum intensity, or wherein the plural pulses of each of the trains comprise a last pulse having a last intensity, wherein the last intensity is lower than the maximum intensity, and wherein the intensities of intermediate pulses between the maximum pulse and the last pulse lower from the maximum pulse to the last pulse.

16. The method of claim 12, wherein each of the trains comprises a first train having a first accumulated intensity and a maximum train having a maximum accumulated intensity, and wherein the maximum accumulated intensity is higher than the first accumulated intensity.

17. The method of claim 12, wherein each of the trains comprises an identical number of pulses and/or an essentially identical train temporal width, or wherein each of the trains comprises an identical number of pulses and/or an essentially identical train temporal width, wherein the train temporal width is in a range from about 0.5 seconds to about 1.5 seconds.

18. The method of claim 12, wherein the trains comprise about ten to about twenty trains per minute.

19. The method of claim 12, wherein each of the plural pulses of the trains comprise an essentially identical pulse temporal width, or wherein each of the plural pulses of the trains comprises an essentially identical pulse temporal width, and wherein the pulse temporal width is in a range from about 160 microseconds to about 220 microseconds.

20. The method of claim 19, wherein the pulse temporal width comprises an increasing portion, in which the intensity is increased, and/or a decreasing portion, in which the intensity is decreased.

21. The method of claim 19, wherein the pulse temporal width comprises an increasing portion, in which the intensity is increased, and a decreasing portion, in which the intensity is decreased, wherein the increasing portion and the decreasing portion together cover at least 60 percent of the pulse temporal width.

22. The method of claim 12, wherein the plural pulses of the trains comprises a frequency in a range from about 15 Hertz to about 25 Hertz.

23. The method of claim 12, wherein the field generator of the induction device comprises an electrode and the spatial field generated by the field generator is an electric field, or a coil design and the spatial field generated by the field generator is an electro-magnetic field.

* * * * *